United States Patent [19]
Osborn

[11] 4,403,514
[45] Sep. 13, 1983

[54] PNEUMOTACHOGRAPH WITH PITOT-LIKE TUBES

[75] Inventor: John J. Osborn, Tiburon, Calif.
[73] Assignee: Critikon, Inc., Tampa, Fla.
[21] Appl. No.: 363,173
[22] Filed: Mar. 29, 1982

Related U.S. Application Data

[63] Continuation of Ser. No. 151,742, May 20, 1980, abandoned.

[51] Int. Cl.³ .............................. G01F 1/36; A61B 5/08
[52] U.S. Cl. ............................. 73/861.52; 73/861.42; 128/725
[58] Field of Search ........... 73/861.42, 861.52, 861.61, 73/861.62, 861.65; 128/725

[56] References Cited
U.S. PATENT DOCUMENTS

| | | | |
|---|---|---|---|
| 2,306,940 | 12/1942 | Fischer | 73/861.61 |
| 2,687,645 | 8/1954 | Velten et al. | 73/861.61 |
| 4,008,611 | 2/1977 | Turocy | 73/861.52 |
| 4,083,245 | 4/1978 | Osborn | 73/861.53 |

Primary Examiner—Herbert Goldstein
Attorney, Agent, or Firm—Audley A. Ciamporcero, Jr.

[57] ABSTRACT

A pneumotachograph including a housing having first and second ports which, during the course of respiration, alternate as input and output ports and which provide a path for generally linear flow of the respiratory gases. A pair of pitot tubes are disposed along the top of the path and are positioned generally at right angles thereto. A pair of baffles or flow deflectors are disposed in the path in alignment with the axes of the pitot tubes. Each of the baffles is positioned at an angle of approximately 45° to the axis of its associated pitot tube and to the path of flow. The baffles may be held in the flow path by a rigid connection or alternatively, they may be retained there by a resilient connection such that the pitot tube measurement is linearized.

In another embodiment, the baffles may actually be merged into a single baffle thus leaving an annular opening between itself and the housing with the opening of the gap being approximately the same distance as the distance between the pair of tubes.

14 Claims, 7 Drawing Figures

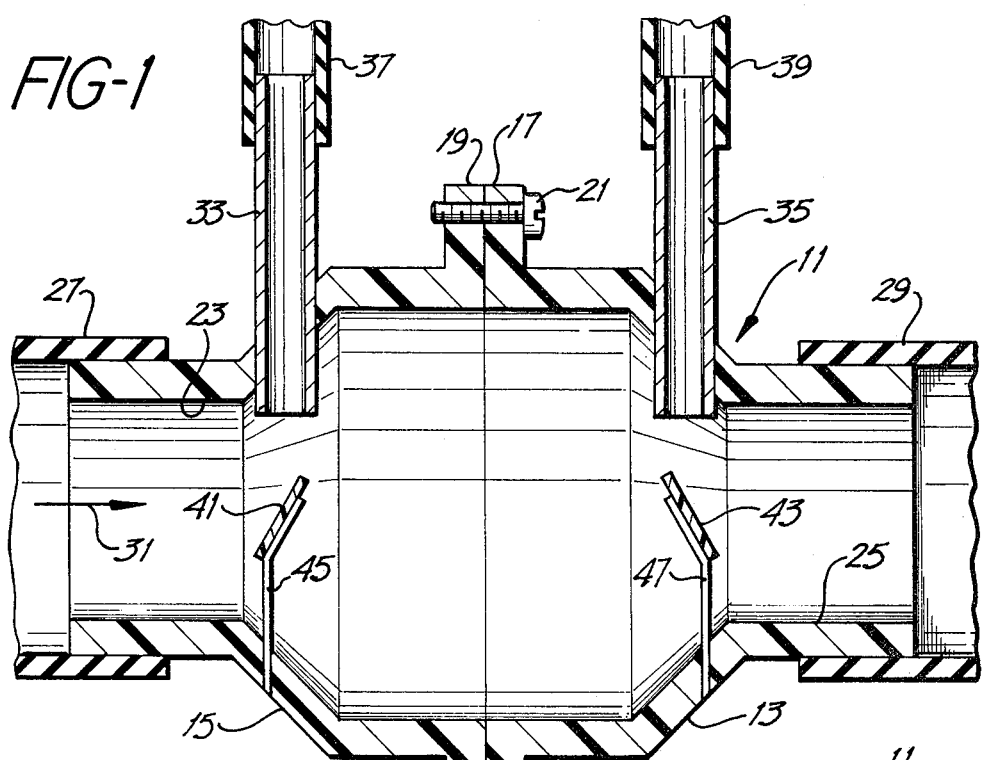
FIG-1
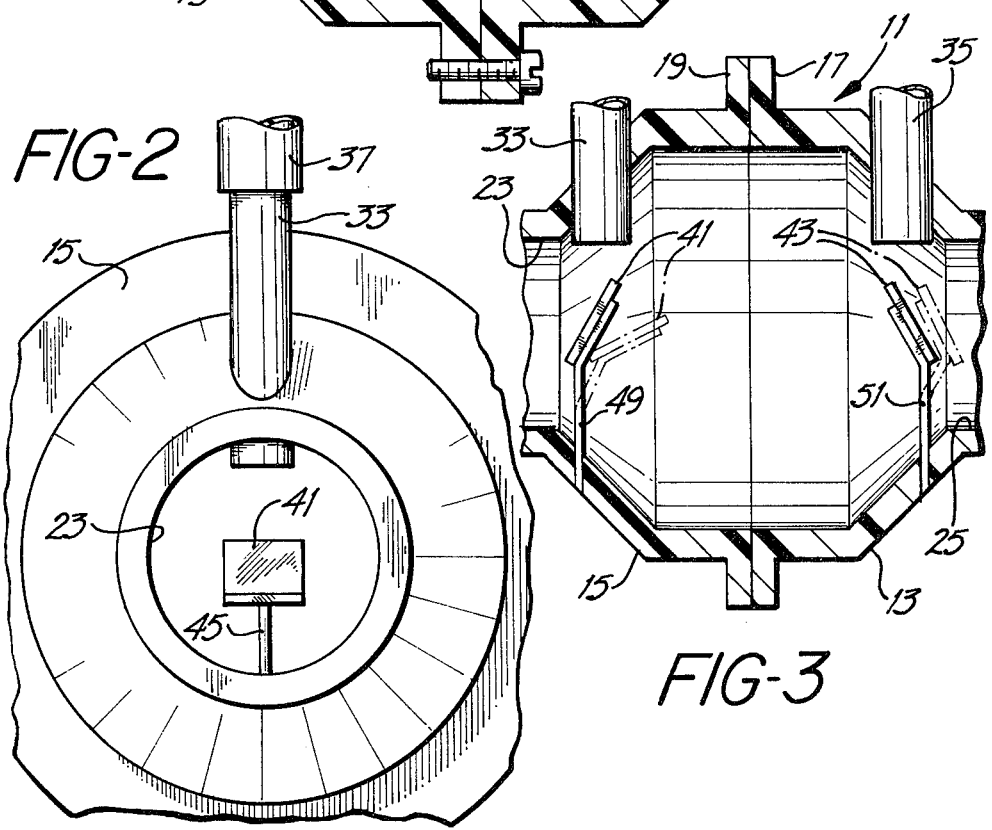
FIG-2
FIG-3

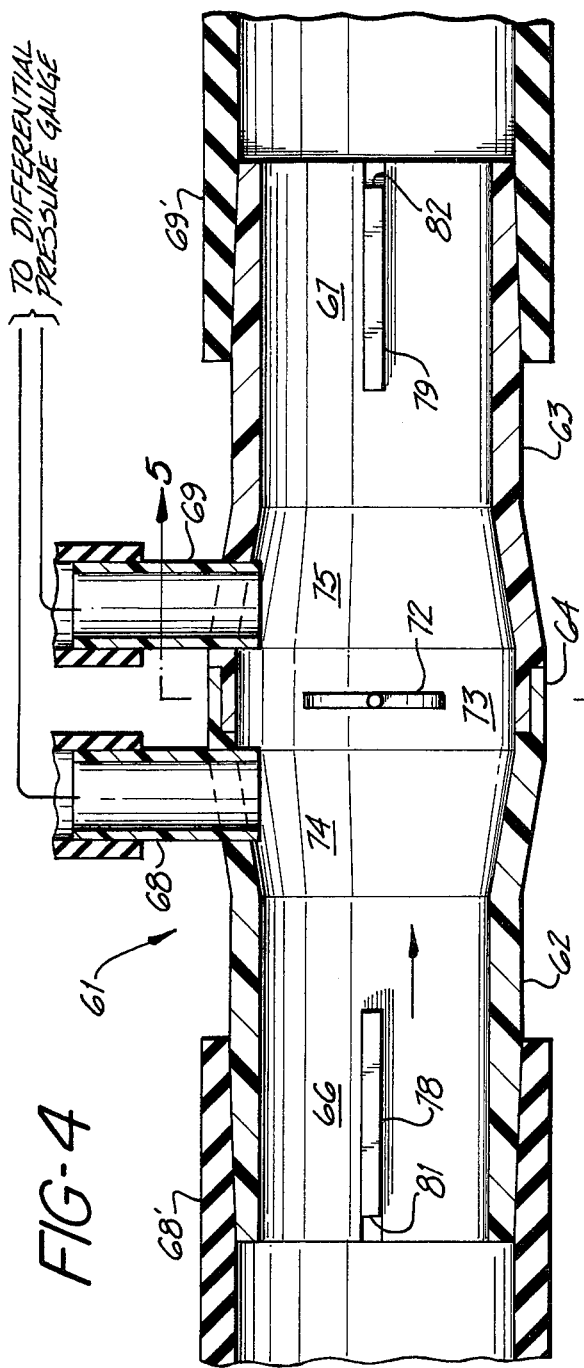
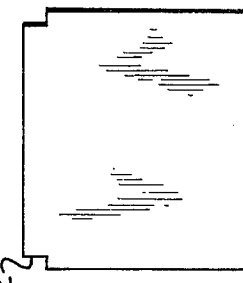
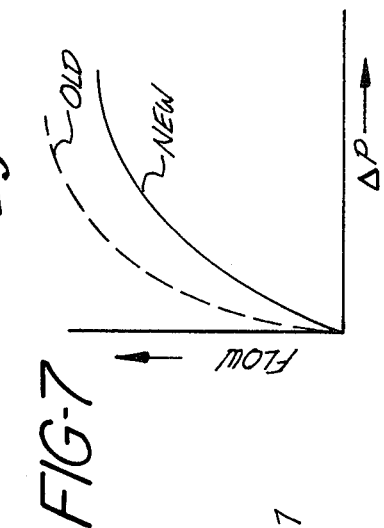
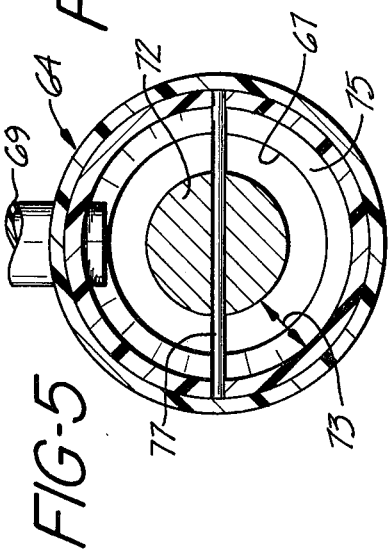

PNEUMOTACHOGRAPH WITH PITOT-LIKE TUBES

This is a continuation of application Ser. No. 151,742, filed May 20, 1980 now abandoned.

Devices for measuring the flow of respiratory gases are well known in the art, and one of such devices is described in applicant's prior issued U.S. Pat. No. 4,083,245, entitled "Variable Orifice Gas Flow Sensing Head." Other such devices include the well known orifice meter pneumotachographs. Although pitot tubes have also been known for many years as a means for measuring flow of gases, pitot tubes have not been successfully used in the measurement of respiratory gases since, as is well known, pitot tubes operate with an orifice directed into the flow of the gas to be measured. With such a configuration, the normally present flecks of mucus and drops of moisture found in respiratory gases have a tendency to enter the pitot tube orifice and to block it. Such blockage, of course, would render the pitot tube inoperative. In one prior attempt to use pitot tubes, a multiplicity of the tubes were employed on the theory that not all of them would be plugged simultaneously. This attempt, however, was unsuccessful.

Both orifice meters and classic pitot tubes, when used for flow measurement, operate on the common principle of a constant area and a variable pressure drop. In the case of orifice meters the pressure drop is created by the resistance of an orifice and is measured by a pair of tubes or "pressure taps." For a respiratory device it is desirable to minimize this resistance. The foregoing patent and an article in *Anesthesiology*, Vol. 51, No. 2, August 1979, by Jaklad et al. entitled "Pneumotachography" discusses this technique. Orifice plates are also discussed in the McGraw-Hill *Encyclopedia of Science and Technology*, 1977, under the heading "Flow Measurement."

In a classic pitot tube the pressure differential is between an "impact" or "stagnation" pressure and a static pressure.

It is a general object of the present invention to provide a pneumotachograph which utilizes pitot like tubes to provide low resistance with high sensitivity and yet avoids the problems of tube blockage from mucus, water or other nongaseous material in the respiratory gases.

The objects of the invention are accomplished by providing a pneumotachograph having a pair of input-output ports defining a flow path for respiratory gases, first and second tubes are disposed along the flow path, and at least one baffle is disposed in the center of the flow path to form an annular like opening and positioned below at least one of the tubes to produce a high pressure on the upstream input side of said flow path in proximity to said tube, the pressure between said first and second tubes being indicative of flow velocity.

Referring to the drawing, FIG. 1 is a cross sectional elevation showing a pneumotachograph in accordance with one embodiment of the invention;

FIG. 2 is an end elevation of the pneumotachograph shown in FIG. 1;

FIG. 3 is a partial cross-sectional elevation similar to FIG. 1 but showing an alternative embodiment of the invention;

FIG. 4 is a cross-sectional elevation showing a pneumotachograph in accordance with another embodiment of the invention;

FIG. 5 is a cross-sectional view taken along the line 5—5 of FIG. 4;

FIG. 6 is a top view of a component of FIG. 4; and

FIG. 7 is a set of characteristic curves showing the improvement in sensitivity of the present invention.

The pneumotachograph shown in FIGS. 1 and 2 includes a housing 11 preferably formed of two sections 13 and 15 connected together by means of mating flanges 17 and 19 and connecting screws 21. The housing includes a pair of input-output ports 23 and 25 which may be connected to flexible tubes 27 and 29, respectively. The tubes 27 and 29 may be connected to a respiratory apparatus and respiratory mask respectively.

Thus it can be seen that, as the patient breathes, during expiration respiratory gases flow in one direction, and upon inspiration the gases will flow in the opposite direction.

Ports 23 and 25 provide a generally linear path of respiratory flow shown generally by the arrow 31. A pair of pitot tubes 33 and 35 are included and extend through the housing walls. Pitot tubes 33 and 35 are connected by means of flexible tubing 37 and 39 to a differential pressure gauge which is not shown but which is well known in the art. Below each of the pitot tubes and in general alignment with the axes thereof are disposed a pair of baffles 41 and 43 which are retained upon standards 45 and 47, respectively. Each of the baffles 41 and 43 is disposed at an angle of gas flow reflection between its associated pitot tube and the direction of the flow path from different ones of the ports 23 and 25. With a linear flow path as shown in FIG. 1, the baffles are ideally disposed at an angle of from 60° to 70° to the flow path. Thus when the port 23 is serving as the input port and the direction of flow is as shown by the arrow 31, a portion of the gases are reflected by the baffle 41 to the pitot tube 33. At this time the baffle 43 reflects none or very little of the gases to its associated pitot tube 35. When the direction of flow reverses, the baffle 43 does reflect a portion of the flow to the pitot tube 35 and the pitot tube 33 becomes passive since the baffle 41 reflects more or very little or the gases to it.

In the embodiment shown in FIG. 1 the standards 45 and 47 are relatively rigid whereby the baffles 41 and 43 are held securely in the position shown in FIG. 1. As can be seen more clearly in FIG. 2 the baffles 41 and 43 may take the form of relatively small flat plates and serve essentially as deflectors. In use, the upstream baffle directs air into one of the pitot tubes which serves as a positive pressure sensor proportional to the flow of gases. The downstream tube would receive none or very little reflected flow and so acts as a passive pressure sensor. During the course of respiration the baffles 41 and 43 alternate as upstream and downstream baffles and so the pitot tubes alternate as positive pressure sensors and passive pressure sensors.

In operation, as the respiratory gases are directed toward the baffles 41 or 43, the gases themselves are directed up toward the pitot tubes 33 or 35 but the heavier flecks of mucus, water or other nongaseous material do not rise so easily and in reality merely run up to and over the top of the baffle falling across the downstream side thereof. Thus the gases which actually reach the pitot tube are relatively clean and do not have any clogging effect.

In the operation of the pneumotachograph of FIG. 1 connected to a differential pressure gauge, the output is not linear but rather is exponential such that the measured differential pressure is an exponential function of velocity of flow (see FIG. 7). Since the relationship between the differential pressure and the velocity of flow is exponential it is a relatively simple matter to linearize with either a microprocessor or even by analog techniques both of which are well known to those skilled in the art.

The pneumotachograph as described above has a substantial advantage over those prior art devices known as orifice meter pneumotachographs in that a higher signal and lower resistance to flow results from the construction. Moreover, the device has no moving parts and is very easy to construct by molding such that mass production of a pneumotachograph for respiratory measurements is economically feasible.

In certain instances it is desirable that the output signal have a linear relationship to the flow without the use of a microprocessor or analog techniques. This relationship can be provided by the embodiment shown in FIG. 3 wherein the baffles 41 and 43 are supported on flexible standards 49 and 51 respectively.

Preferably the standards 49 and 51 are formed of Kapton plastic having a thickness of 3 mils. With such a construction the measured differential pressure signal varies linearly with the flow of fluid through the pneumotachograph regardless of the velocity. Thus as velocity is increased from left to right, as shown in FIG. 3, the standards 49 and 51 flex so that they and the baffles supported thereby move to the position shown in dash-dot lines thus decreasing the amount of gases reflected to the pitot tube 33 and permitting some of the bases to be reflected to the pitot tube 35. Thus, the positive signal produced by the pitot tube 33 is decreased whereas, at the same time, the signal at the pitot tube 35 which is essentially zero when in the position shown in solid lines in FIG. 3, shifts toward the positive. The correction provided by the movement of the baffles 41 and 43 is itself exponential and thus cancels out the exponential variation in the differential pressure signal from the two tubes.

The pneumotachograph shown in FIGS. 4 and 5 includes a housing 61 formed of left and right sections 62 and 63 connected together by male and female portions at 64. The housing includes a pair of input/output ports 66 and 67 which may be connected to flexible tubes 68' and 69', respectively. In the embodiment of FIG. 1, these tubes may be connected to a respiratory apparatus and respiratory mask, respectively. A pair of tubes 68 and 69 are included and extend through the housing walls so that their axes is perpendicular to the nominal flow path of gases indicated by the arrow 71. Tubes 68 and 69 are connected to a differential pressure gauge is indicated.

A disc-shaped baffle 72 is disposed in the center of the flow path 71 and perpendicular to it to form an annular-like opening 73, see especially FIG. 5, between the cylindrical housing 61 and the disc-shaped baffle 72. It is suspended from the walls of the housing by a fixed rod 77. Moreover it is positioned substantially below the bottom openings of the tubes 68 and 69 so that on the upstream side, that is, at 74 assuming the flow in in the direction 71, a high pressure is produced in the proximity to the end of tube 69. In addition, a low pressure is produced at 75 on this downstream side because of a venturi effect.

In accordance with flow measurement theory, the pressure difference between the two tubes in indicative of flow velocity. This is more specifically indicated in FIG. 7, where the pressure differential, delta P, is the horizontal axis and FLOW the vertical axis.

The non-linear curve labeled "NEW" is very similar to that produced by the embodiment of FIG. 4 and is easily compensated for by the microprocessor techniques. The other curve labeled "OLD" indicates prior techniques, especially orifice techniques, where at low flow rates, because of the steeper curve, the sensitivity of the gauge is greatly reduced. Thus, FIG. 7 aptly illustrates the improvement of the embodiment of FIG. 4 in increased small signal sensitivity compared to an equivalent orifice meter with the same flow resistance.

The present invention also has the advantage of a greater signal to noise ratio. The venturi effect mentioned as a probable cause of a lower pressure at the locality 75 in proximity to tube 69 is perhaps not the total cause of the low pressure. In general comparing the embodiments of FIGS. 1 and 4, FIG. 4 might be considered as a scaleddown reflected pitot design where the two reflectors 41 and 43 have been merged into one baffle. It is also believed that if the baffles 41 and 43 of FIG. 1 are made vertical, 70% of the "reflected" effect will be retained. Thus, the tubes 68 and 69 of FIG. 4 might be called pitot-like tubes in one sense or pressure taps in the sense of standard orifice meter; or the present invention might be thought of as a hybrid between a standard orifice meter and a standard pitot tube measuring device. In any case, it is not intended that the invention be unduly limited by the standard definition of a pitot tube which extends directly into the flow of gas to be measured.

In order to insure that the flow of gas is relatively stable, that is, a misapplied input tube 68 might cause an unwanted jet effect where the flow is not uniform over its cross-section, a pair of flow director horizontal plates 78 and 79 are provided. FIG. 6 is an elevation view of both of these plates. They are affixed to notches in the side walls of housing halves 62 and 63 with an end notch 81 and 82, respectively, ensuring against slippage out of the structure and into the breathing way of the patient. The flow director plates, of course, are horizontal and co-planar with the flow path 71 and provide stable flow.

An orifice measuring device with a center plate such as 72 has been suggested. For example, see the Fourth Edition of Perry's *Encyclopedia of Chemical Engineering* where annular orifice meters are discussed. These apparently are used only in industrial applications and the pressure tap on the downstream side is far enough away from the baffle so as not to be affected by any venturi action. In comparison in the present invention which, of course, must be set up for bi-directional flow, the spacing of the tubes with respect to their outer diameters is approximately the same as the annular opening 73. This is believed to cause the pressure build-up on the upstream side and the lower pressure on the downstream side which provides a significant differential downstream side which provides a significant differential pressure. In fact, there is enough of a pressure difference, which increases sensitivity, that for a readable signal which is obtained from the differential pressure gauge, the resistance to air flow is only half the amount of an equivalent orifice meter. As in the case of FIG. 1, the embodiment of FIG. 4 avoids the problem of tube blockage by mucus, water or other non-gaseous material carried by respiratory gases. In addition the construction of FIG. 4 is smaller and has less dead-space.

What is claimed is:

1. A pneumotachograph comprising a housing having a pair of input-output ports defining a flow path for respiratory gases, first and second pitot tubes disposed along said flow path and a pair of baffles disposed in said flow path and below each of said pitot tubes, each of said baffles being disposed at an angle of gas flow reflection between the axis of its associated pitot tube and the flow path from a different one of said ports.

2. A pneumotachograph as defined in claim 1 wherein said flow path is linear.

3. A pneumotachograph as defined in claim 2 wherein said baffles are disposed at an angle of from 60° to 70° to said flow path.

4. A pneumotachograph as defined in claim 1 wherein said baffles are flat plates.

5. A pneumotachograph as defined in claim 1 wherein said baffles are rigidly disposed in said flow path.

6. A pneumotachograph as defined in claim 1 together with a flexible standard supporting each of said baffles in said flow path whereby upon increased flow of respiratory gases therethrough the angle between said baffles and the axes of their associated pitot tubes is varied.

7. A pneumotachograph comprising a housing having a pair of input-outputs ports defining a flow path for respiratory gases, one of said ports defining an inspiration input port and the other of said ports defining an expiration input port, first and second pitot tubes disposed along said flow path and at right angles thereto, and a pair of baffles disposed in said flow path, one of said baffles being disposed at an angle of reflection between the axis of one of said pitot tubes and the direction of said flow path from said inspiration input port, the other of said baffles being disposed at an angle of reflection between the axis of the other of said pitot tubes and the direction of said flow path from said expiration input port.

8. A pneumotachograph as defined in claim 7 wherein said flow path is linear.

9. A pneumotachograph as defined in claim 8 wherein said baffles are disposed at an angle of from 60° to 70° to said flow path.

10. A pneumotachograph as defined in claim 7 wherein said baffles are flat plates.

11. A pneumotachograph as defined in claim 7 wherein said baffles are rigidly disposed in said flow path.

12. A pneumotachograph as defined in claim 7 together with a flexible standard supporting each of said baffles in said flow path whereby upon increased flow of respiratory gases therethrough the angle between said baffles and the axes of their associated pitot tubes is varied.

13. A bidirectionally operative pneumotachograph comprising:
   a housing having a pair of respectively interchangeable input-output ports defining a flow path for respiratory gases,
   a pair of spaced apart tubes disposed along said flow path, at right angles thereto, and communicating with, and penetrating into said flow path by a small, distance; and
   a flat, disc shaped baffle disposed in the center of said flow path and perpendicular thereto to form an annular like opening between said baffle and said housing for said gases, said baffle being positioned between said tubes to produce a high pressure in proximity to the upstream tube and a low pressure in proximity to the downstream tube, the pressure differential between said tubes being indicative of flow velocity, wherein the spacing of said tubes is approximately the same as the radial dimension of said annular like opening, whereby increased differential pressure between said tubes is promoted regardless of the direction of flow through said path.

14. A pneumotachograph as described in claim 13 and further including a pair of horizontal flow director plates spanning said housing, coplanar with the flow path, adjacent both ports whereby stable flow is provided.

* * * * *

UNITED STATES PATENT AND TRADEMARK OFFICE
CERTIFICATE OF CORRECTION

PATENT NO. : 4,403,514

DATED : September 13, 1983

INVENTOR(S) : John J. Osborn

It is certified that error appears in the above-identified patent and that said Letters Patent are hereby corrected as shown below:

column 5, line 27 "outputs" should be --output--.

Signed and Sealed this

Seventh Day of August 1984

[SEAL]

Attest:

GERALD J. MOSSINGHOFF

Attesting Officer

Commissioner of Patents and Trademarks